(12) United States Patent
Green et al.

(10) Patent No.: US 9,205,167 B2
(45) Date of Patent: Dec. 8, 2015

(54) DISPENSER SYSTEM FOR AEROSOL AND NON-AEROSOL PRODUCTS

(71) Applicant: Kimberly-Clark Worldwide, Inc., Neenah, WI (US)

(72) Inventors: Jonathan Green, Surrey (GB); Peter W. Yeme, Peterborough (GB); Christopher Bleasby, Cambridge (GB)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 40 days.

(21) Appl. No.: 14/268,674

(22) Filed: May 2, 2014

(65) Prior Publication Data

US 2015/0314032 A1 Nov. 5, 2015

(51) Int. Cl.
| | |
|---|---|
| *B67D 1/00* | (2006.01) |
| *A61L 9/14* | (2006.01) |
| *B65D 83/38* | (2006.01) |
| *B05B 11/00* | (2006.01) |

(52) U.S. Cl.
CPC ............... *A61L 9/14* (2013.01); *B05B 11/0037* (2013.01); *B65D 83/384* (2013.01)

(58) Field of Classification Search
CPC .. B65D 83/384; B65D 83/386; B65D 83/388; B05B 11/0037; A61L 9/14
USPC ............ 222/61, 63, 645, 649, 173, 626, 183, 222/184, 504, 333; 239/71, 380, 381
See application file for complete search history.

(56) References Cited

U.S. PATENT DOCUMENTS

| | | | |
|---|---|---|---|
| 3,589,563 A * | 6/1971 | Carragan et al. ............... | 222/648 |
| 4,084,732 A | 4/1978 | Dearling | |
| 4,601,886 A | 7/1986 | Hudgins | |
| 5,249,718 A * | 10/1993 | Muderlak ...................... | 222/642 |
| 5,383,580 A * | 1/1995 | Winder ......................... | 222/325 |
| 5,565,148 A | 10/1996 | Pendergrass, Jr. | |
| 5,772,074 A * | 6/1998 | Dial et al. .......................... | 222/1 |
| 6,267,297 B1 * | 7/2001 | Contadini et al. ................ | 239/1 |
| 6,517,009 B2 | 2/2003 | Yahav | |
| 6,610,254 B1 | 8/2003 | Furner et al. | |
| 6,802,460 B2 | 10/2004 | Hess et al. | |
| 7,222,760 B1 * | 5/2007 | Tsay ............................. | 222/642 |
| 7,597,308 B1 | 10/2009 | Stucki | |
| 7,798,424 B2 * | 9/2010 | Lin ................................. | 239/305 |
| 7,905,229 B2 | 3/2011 | Giroux et al. | |
| 8,170,405 B2 | 5/2012 | Harris | |

(Continued)

FOREIGN PATENT DOCUMENTS

EP 2 047 868 A2 4/2009

OTHER PUBLICATIONS

F-MATIC Flex Air Freshener Dispenser, AeroScents, Inc., Natural Odor Eliminating Products, Internet web page "http://www.aeroscents.com/F-MATIC-Flex-Air-Freshener-Dispenser-AE100.htm", viewed and printed May 7, 2014, 2 pages.

*Primary Examiner* — Lien Ngo

(57) ABSTRACT

A dispensing system for air care products contained in aerosol and non-aerosol containers having spray nozzles includes a dispenser including a contoured surface that is configured to accept an aerosol container within the interior of the dispenser, the dispenser further including an adaptor releasably attached to the contoured surface of the dispenser, the adaptor configured to retain a non-aerosol container within the interior of the dispenser such that the actuator may contact the non-aerosol spray nozzle.

9 Claims, 14 Drawing Sheets

(56) References Cited

U.S. PATENT DOCUMENTS

| | | | |
|---|---|---|---|
| 8,342,369 B2* | 1/2013 | Hsu | 222/309 |
| 8,573,443 B2* | 11/2013 | Natterer | 222/52 |
| 8,889,082 B2* | 11/2014 | Muderlak et al. | 422/306 |
| 2006/0144851 A1 | 7/2006 | Gonzalez | |
| 2008/0156896 A1 | 7/2008 | Anderson et al. | |
| 2010/0226818 A1 | 9/2010 | Miyagi et al. | |
| 2012/0048959 A1 | 3/2012 | Maas et al. | |
| 2012/0199612 A1 | 8/2012 | Demarest et al. | |

* cited by examiner

DISPENSER SYSTEM FOR AEROSOL AND NON-AEROSOL PRODUCTS

FIELD OF THE INVENTION

The present invention relates generally to the field of dispenser systems which are capable of dispensing aerosol or non-aerosol products, and more particularly to dispenser systems which are capable of being easily adapted to dispense either aerosol or non-aerosol products.

BACKGROUND OF THE INVENTION

Products that are delivered in aerosol spray containers are generally not favored by purchasers when compared to non-aerosol spray or 'pump' containers. This preference may be caused by higher costs of certain aerosol containers or concerns over a negative environmental impact of the aerosols due to the difficulty of recycling these containers. Additionally, there is concern that some aerosol containers continue to include chlorofluorocarbons (CFCs) and volatile organic compounds (VOCs). Both CFCs and VOCs are viewed as harmful to the environment.

In locations such as airports, office buildings, hotels and public buildings, dispensers may be installed which only accept aerosol containers. Aerosol spray containers deliver a suspension of fine particles (solid or liquid) in a gas under pressure. When the spray nozzle of the aerosol container is depressed, the pressurized suspension is released into the air propelled by the gas. Non-aerosol or pump spray containers are packaged as a liquid and are emitted as small droplets propelled in short bursts. This difference in delivery of the material from the container creates a barrier to using a dispenser that is configured to dispense materials from an aerosol container to dispense materials from a non-aerosol container. Additionally, the removal and replacement of these dispensers can be costly and time-consuming.

The present invention provides a dispenser system which permits products to be dispensed from either aerosol or non-aerosol containers from the same dispenser. In some instances, a dispenser that was originally configured to dispense materials from aerosol containers may be reconfigured to dispense materials from non-aerosol containers. The present invention may also be utilized to simplify the manufacture of dispensers so that similarly designed dispensers may be easily configured to dispense materials from either aerosol or non-aerosol containers.

SUMMARY OF THE INVENTION

Objects and advantages of the invention will be set forth in part in the following description, or may be obvious from the description, or may be learned through practice of the invention.

The present invention is directed to a dispensing system for products which may be dispensed into the air from aerosol containers or non-aerosol containers. Both aerosol and non-aerosol containers include a spray nozzle. Aerosol containers are generally cylindrical and the cylinder forms a reservoir for the material to be dispensed. The spray nozzle is positioned atop the cylinder and, in many embodiments, the cylinder tapers inwardly proximate to the spray nozzle. Non-aerosol containers come in a wide variety of forms and generally include a reservoir formed of plastic, metal or a combination of materials which may or may not be flexible. The non-aerosol containers typically contain a collar which connects the reservoir to the stem on which the spray nozzle is positioned. The collar may include internal features which cause the material within the reservoir to atomize upon expulsion from the reservoir.

The dispensing system may include a dispenser that has an interior formed by a front cover, a back cover and a base. A wide range of dispensers having many different features are suitable for use in the present invention. An actuator is preferably positioned within the dispenser and functions to depress the spray nozzle of aerosol containers and non-aerosol containers. The actuator may be variously configured to perform its function and may, in some embodiments, be configured as a pivoting lever that is spring-biased into a position which causes dispensing of material from the container.

The dispenser also includes a controller which initiates a dispensing cycle and causes the actuator to depress the spray nozzle. The controller may be electrical, mechanical or electro-mechanical and may permit the dispensing of material at predetermined time intervals. Many commonly available dispensers include actuators and controllers which are suitable for use in the present invention.

The dispenser includes a selection switch that is positionable in either an aerosol dispensing position or a non-aerosol dispensing position. In certain embodiments of the dispenser, the selection switch may be positioned in the interior of the dispenser or the interior of the controller. When the selection switch is in the non-aerosol dispensing position, the selection switch may alter the function of the actuator which changes the manner in which the actuator acts upon the spray nozzle. In some embodiments, this alteration results in the spray nozzle of the non-aerosol containers being moved downward a differing amount than the spray nozzle for aerosol containers.

The dispenser also includes a contoured surface that is configured to accept an aerosol container and, in some embodiments, is configured to accept the tapered upper portion of the cylinder. The aerosol container is positioned within the interior of the dispenser such that the actuator may contact the aerosol spray nozzle.

The system of the present invention also includes an adaptor configured to be permanently or releasably attached to the contoured surface of the dispenser. The adaptor may be configured to permit a non-aerosol container to be positioned within the interior of the dispenser such that the actuator may contact the non-aerosol spray nozzle.

In selected embodiments of the invention, the adaptor may be releasably connected to the contoured surface of the dispenser by a retention mechanism. In certain embodiments, the retention mechanism may include a spring arm positioned on the adaptor and an opening formed in the dispenser which engages the spring arm when the adaptor is correctly engaged to the contoured surface.

The dispensing system may utilize an actuator that includes an actuator arm positioned above the spray nozzle so that the actuator arm contacts the spray nozzle as the actuator arm moves downward. In such embodiments, when the selection switch is in the non-aerosol dispensing position it contacts the actuator arm to limit its the downward movement.

The adaptor may have many features which interact and interlock with the non-aerosol container and may include a retainer for accurately positioning the non-aerosol container within the dispenser.

The dispensing system is configured so that it is capable of dispensing material from a non-aerosol container positioned at least partially within the adaptor while the adaptor is retained within the contoured surface and when the selection switch is positioned in the non-aerosol dispensing position.

The present invention is also directed to a dispensing system for air care products which are contained in aerosol containers and non-aerosol containers, the dispensing system including a dispenser having an interior formed by a front cover, a back cover and a base and a contoured surface configured to accept an aerosol container having a spray nozzle within the interior of the dispenser. The dispenser also includes an actuator including an actuator arm positioned above the aerosol or non-aerosol container, the actuator arm moveable between an upper position and a lower position. A controller is included in the dispenser and is adapted to actuate the actuator and move the actuator arm toward the lower position and into contact with the spray nozzle to move the spray nozzle downward and dispense material. An adaptor is configured to be positioned within or in contact with the contoured surface and is configured to retain a non-aerosol container having a spray nozzle within the interior of the dispenser so that the actuator arm will contact the spray nozzle of the non-aerosol container. A selection switch is also part of the present invention and is positionable in an aerosol dispensing position and a non-aerosol dispensing position, the selection switch in the non-aerosol dispensing position contacts the actuator arm to limit the downward movement of the actuator arm. The dispenser system is capable of dispensing material from an aerosol container when the selection switch is positioned in the aerosol dispensing position and also dispensing material from a non-aerosol container positioned at least partially within the adaptor while the adaptor is retained within the detent when the selection switch is positioned in the non-aerosol dispensing position.

The invention will be described in greater detail below by reference to particular embodiments illustrated in the drawings.

DETAILED DESCRIPTION

Reference will now be made in detail to embodiments of the invention, one or more examples of which are illustrated in the figures. Each example is provided by way of explanation of the invention, and not meant as a limitation of the invention. For example, features illustrated or described as part of one embodiment may be used with another embodiment to yield still a further embodiment. It is intended that the present invention include modifications and variations to the embodiments described herein as well as other modifications that are within the scope and spirit of the invention.

Figure 1:
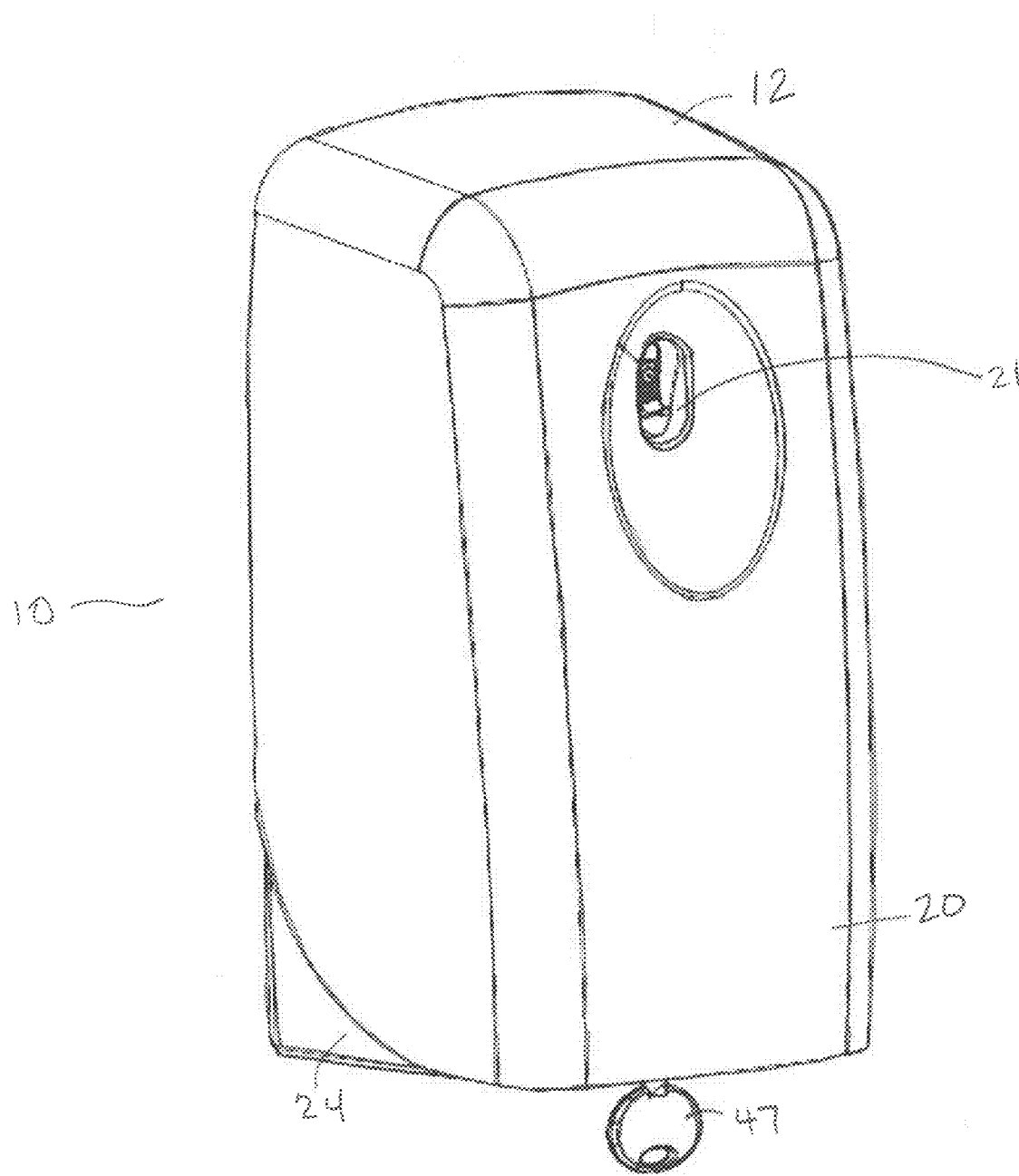
FIG. 1 is a perspective view of an embodiment of the dispenser system of the present invention.
Figure 2:
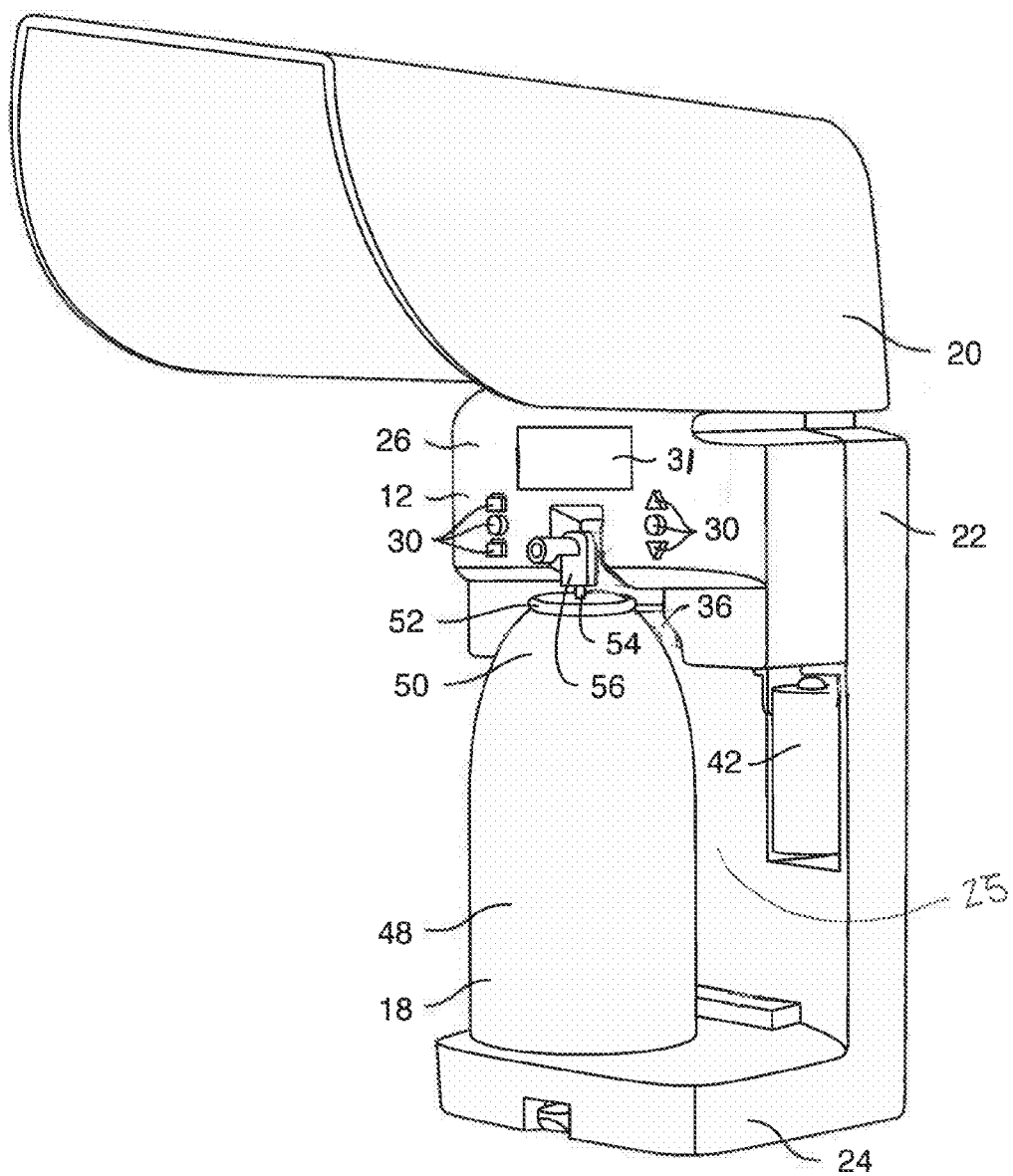
FIG. 2 is a perspective view of an embodiment of a dispenser suitable for use in the present invention, the dispenser shown in its open position and configured to dispense material from an aerosol container.

The present invention is directed to a dispensing system 10 for air care products which are contained in either aerosol containers or non-aerosol containers. An embodiment of the dispensing system 10 is shown in FIG. 1 and includes a dispenser 12 having a front cover 20, a base 24 and an opening 21 formed in the front cover 20 to permit the delivery of material exteriorly of the dispenser 12. In FIG. 2, the dispenser 12 is shown with the front cover 20 in an open position showing the interior 25 of the dispenser that is formed by the front cover 20, a back cover 22 and the base 24.

Referring to FIGS. 2 and 14-16, an aerosol container 18 is positioned within the interior 25 of the dispenser 12 and generally includes a cylinder 48 that functions as a reservoir for materials to be dispensed. As depicted in FIG. 2, the aerosol container 18 is not fully seated within the dispenser 12 so that varying features of the dispenser may be shown. The cylinder 48 includes an upper portion 50. The upper portion 50 may be tapered or otherwise contoured so that its diameter is less than the diameter of the cylinder 48. A spray nozzle 56 is positioned on a narrow stem 54 that extends out of the cylinder 48. In some embodiments of the aerosol container 18, a ring 52 may be positioned between the upper portion 50 and the stem 54. The material to be dispensed from the aerosol container is held within the cylinder 48.

The dispenser 12 includes a controller 26 having a contoured surface 36 which is configured to permit the upper portion 50 and spray nozzle 56 to be seated at least partially within the controller 26. The contoured surface 36 may, in alternate embodiments, be formed as part of a different element of the dispenser 12 and still enable the aerosol container 18 to engage the actuator 32.

Figure 3:
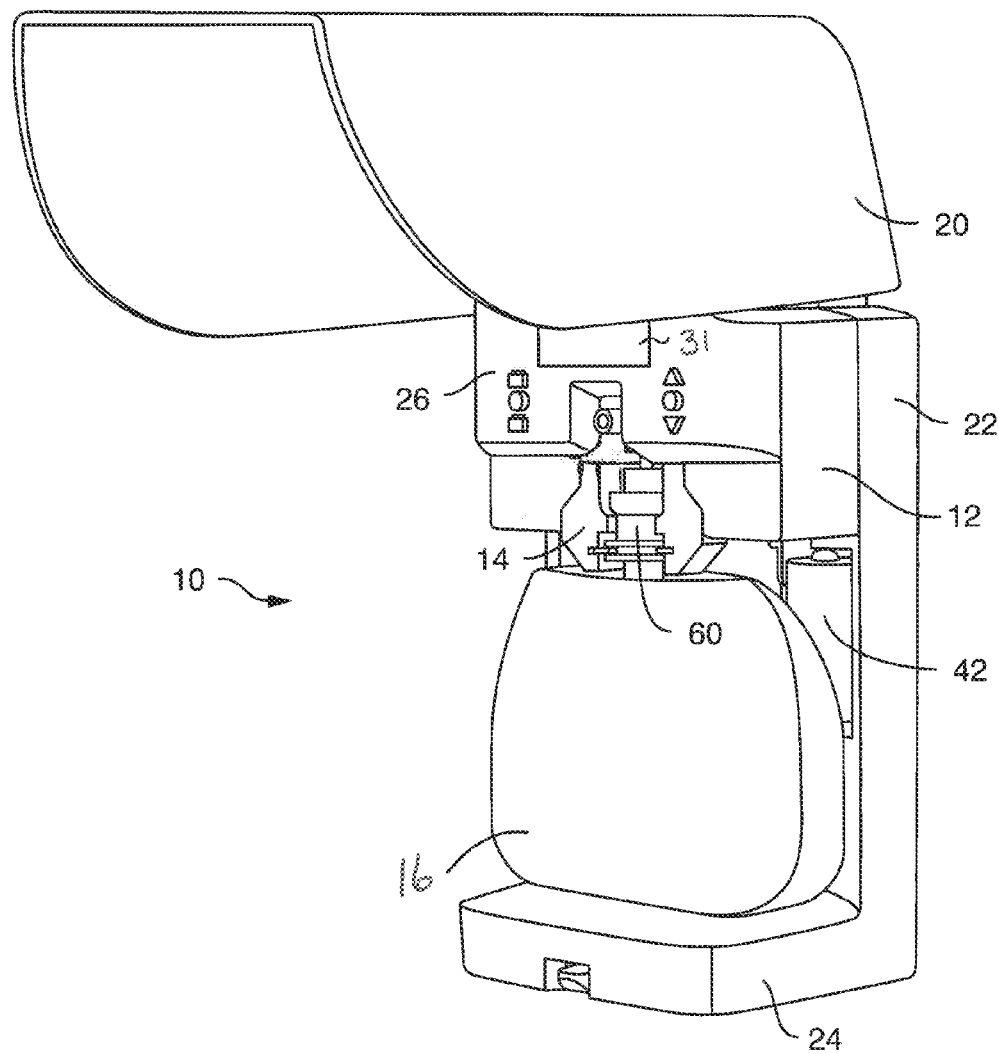
FIG. 3 is a perspective view of an embodiment of the dispenser of the present invention shown in its open position and configured to dispense material from a non-aerosol container.
Figure 12:
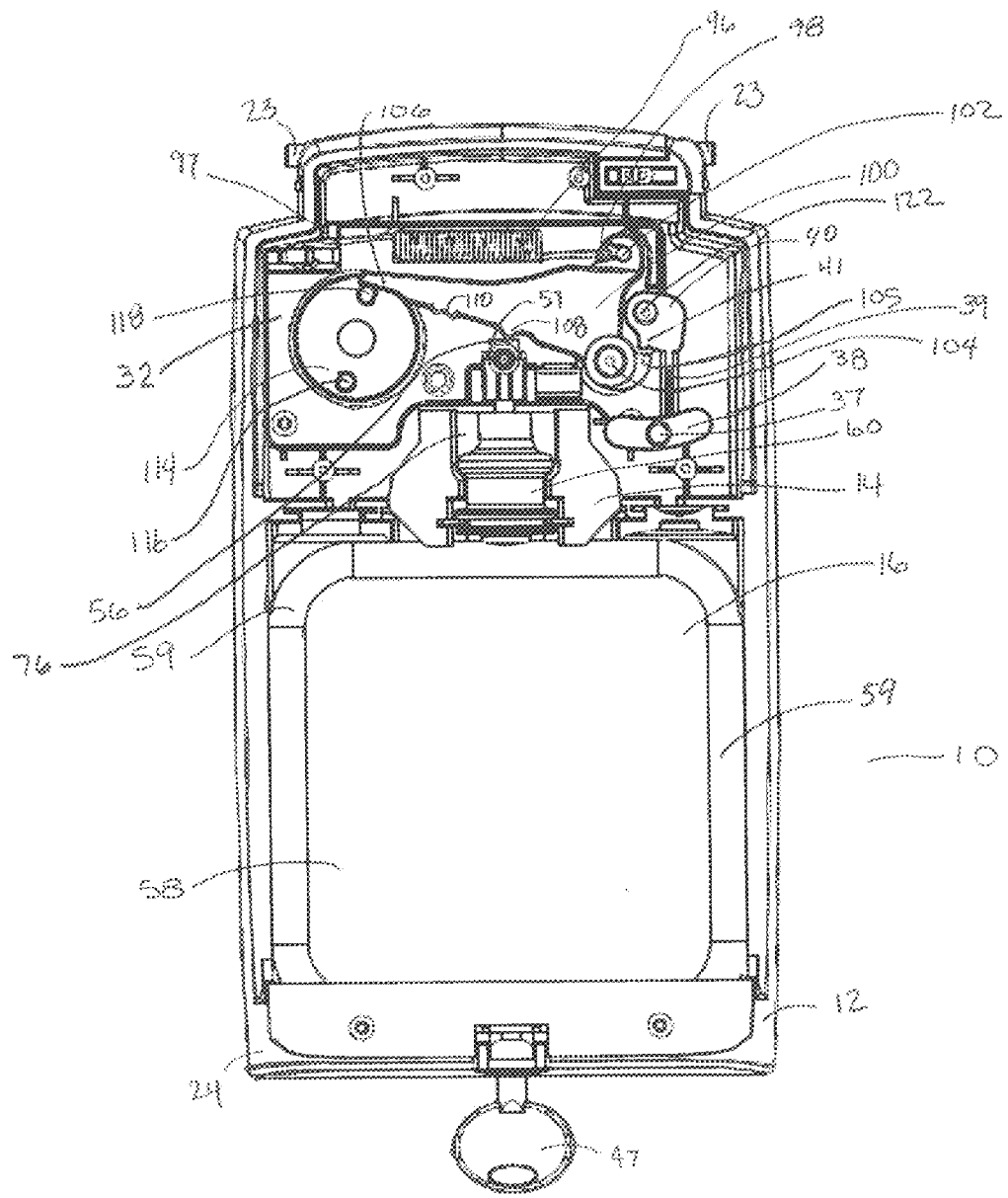
FIGS. 12 and 13 are partial front views of the dispenser system including the dispenser, a non-aerosol container, an adapter and the actuator.
Figure 13:
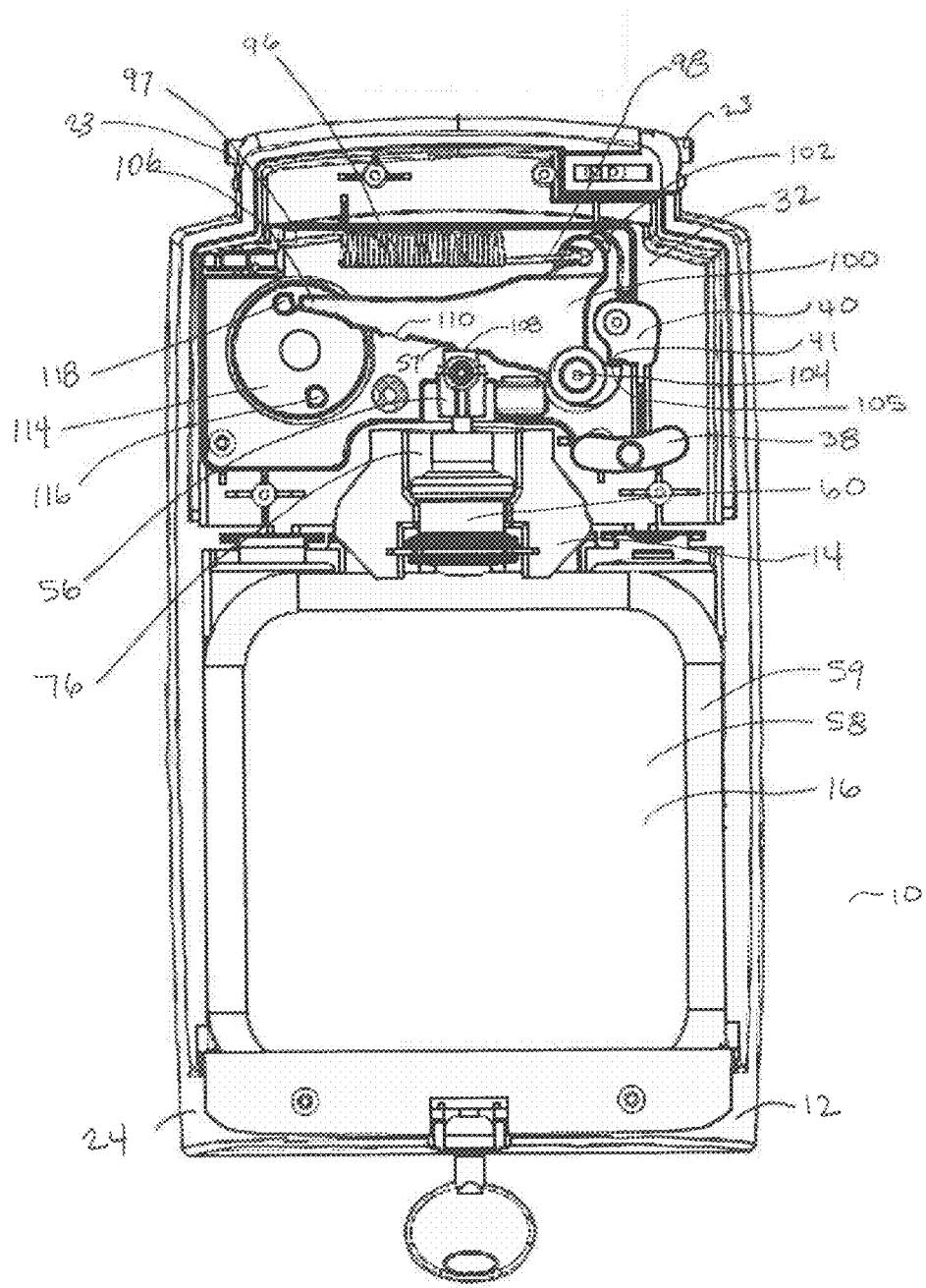

As seen in FIGS. 3, 12 and 13, a non-aerosol container may be used in the dispenser system 10 by attaching an adaptor 14 to the contoured surface 36, the adapter 14 configured so that a non-aerosol container 16 can be properly positioned and retained within the dispenser 12 and material dispensed therefrom.

Figure 4:
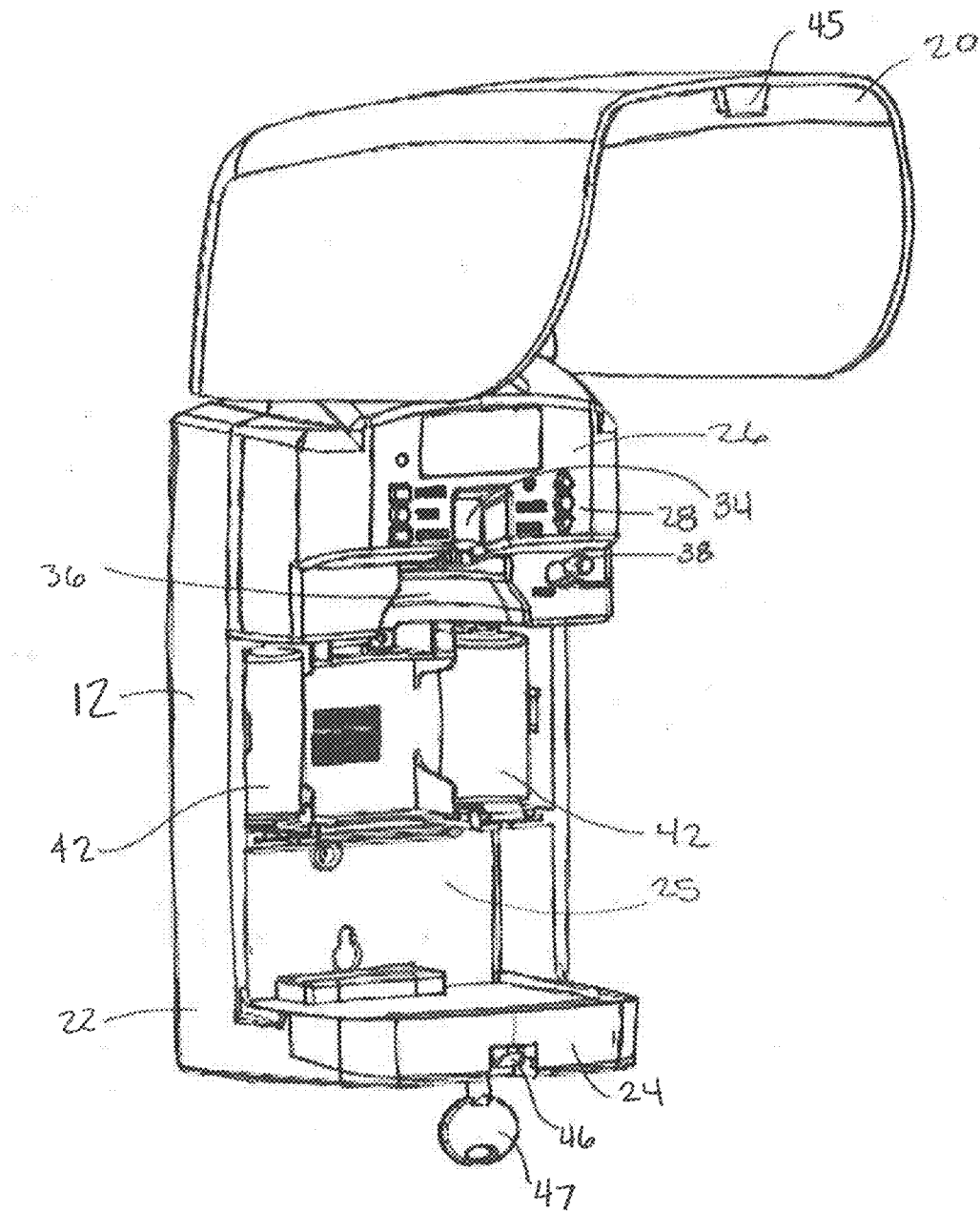
FIG. 4 is a perspective view of an embodiment of the dispenser of the present invention.

Referring now to FIG. 4, an exemplary dispenser 12 is shown and includes an interior 25 and controller 26 within which may be formed the contoured surface 36 and, in some embodiments, a notch 34 positioned above the contoured surface 36. Alternately, the notch 34 may be formed as part of the contoured surface 36. The spray nozzle 56 of each aerosol and non-aerosol container is positioned within the notch 34 enabling a person to see the interaction between the spray nozzle 56 and other components of the dispenser 12. Positioned on the controller is a selection switch 38 which is moveable between an aerosol and a non-aerosol position.

Other features of the dispenser 12 may include a hook 45 and latch 46 which operate to retain the front cover 20 in a closed position. A locking mechanism (not shown) and key 47 may be provided for security.

FIGS. 5-9 show features of an embodiment of the adapter 14 in more detail. While the adapter described is useful in the dispenser 12 described herein, the adapter 14 may be variously configured to modify a dispenser configured to dispense materials from aerosol containers to dispense materials from non-aerosol containers. The adapter 14 generally includes an exterior surface 84 and an interior surface 78. The exterior surface 84 may be configured to conform at least in part to the contoured surface 36 of the dispenser 12, regardless of which feature includes the contoured surface 36.

The adapter 14 preferably includes a retention mechanism by which the adapter is securely retained within the dispenser 12. In the embodiment depicted in FIGS. 8 and 9, the adapter 14 includes a spring arm 92 which is configured to lock the adapter into position within the dispenser 12 by engaging an opening 94. The spring arm 92 and the opening 94 act as a retention mechanism however other types of retention mechanisms including but not limited to press-fitting the adapter 14 to the dispenser 12 may be used in the present invention.

Figure 5:
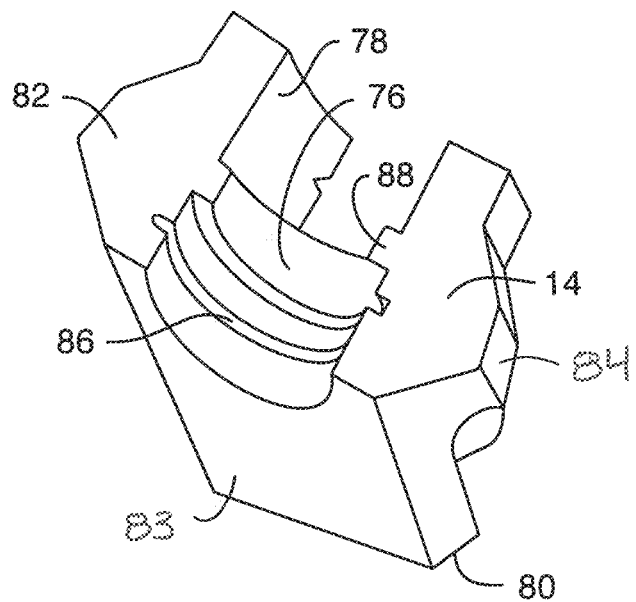
FIG. 5 is a perspective view of an embodiment of the adapter of the present invention.
Figure 6:
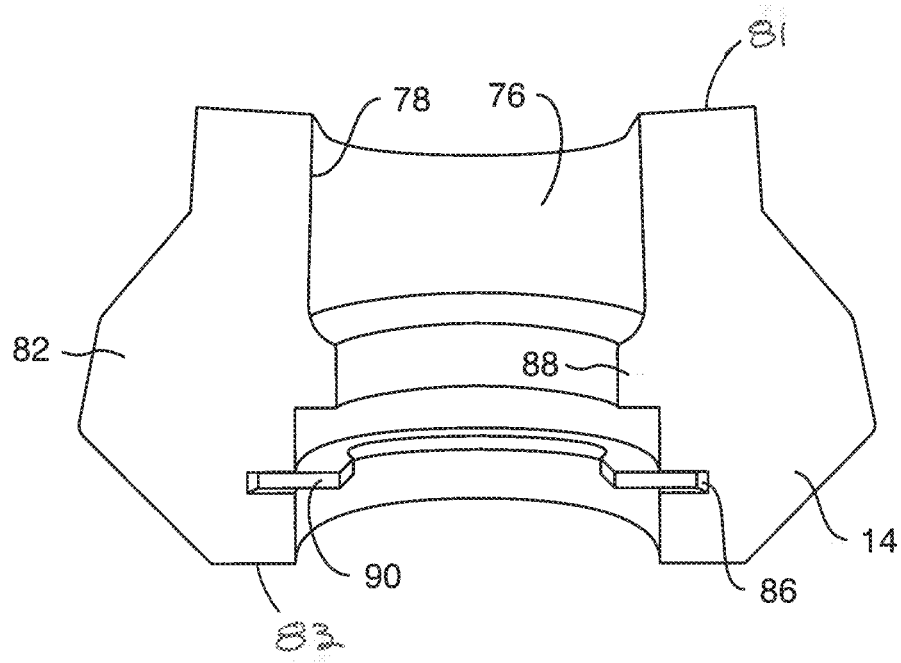
FIG. 6 is an end view of the embodiment of the adapter shown in FIG. 5 and including a support member.

Referring to FIGS. 5 and 6, the adapter 14 may include a first end 80 and a second end 82. The interior surface 78 may include different features to retain any of a number of variously configured non-aerosol containers within the adapter 14. In some embodiments, a retention channel 76 is preferably positioned on the second end 82 and may extend from the top surface 81 of the adapter through the bottom surface 83 of the adapter 14. A ridge 88 is shown in FIGS. 5 and 6 extending around the circumference of the retention channel 76. In selected embodiments the ridge 88 may extend fully around the retention channel 76 or may be formed of a plurality of individual ridges. The ridge 88 may additionally extend only partially around the circumference of the retention channel 76.

Figure 8:
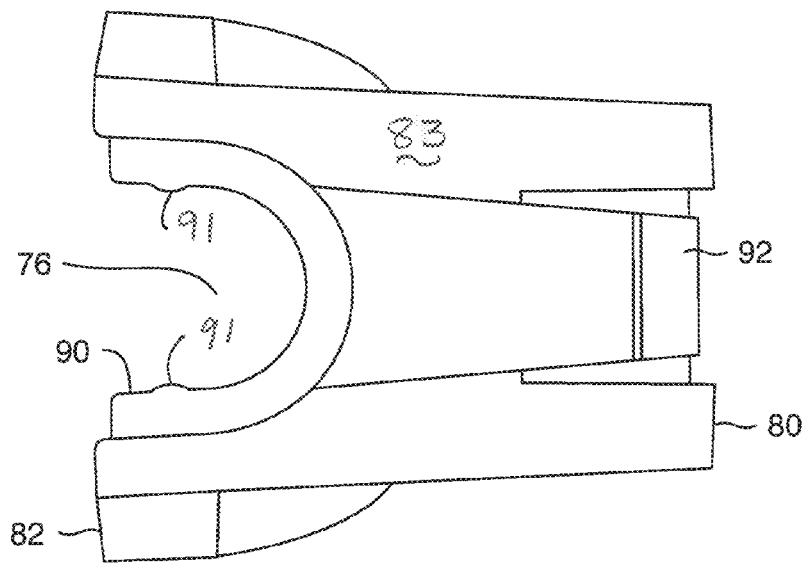
FIG. 8 is a bottom view of the embodiment of the adapter shown in FIG. 7.

A groove 86 may be positioned below the ridge 88 and configured to retain a support member 90. The support member 90 is preferably formed of a rather rigid material and, in some embodiments, may be formed of metal. The support member 90 may be configured so that it is secured within the groove 86 by a number of different mechanisms, such as, for example, press-fit or adhesive. The embodiment of the support member 90 shown in FIG. 8 illustrates that the support member 90 may include one or more retention features such as projections 91. Such retention features may help to retain the non-aerosol container 16 within the adapter 14.

Figure 7:
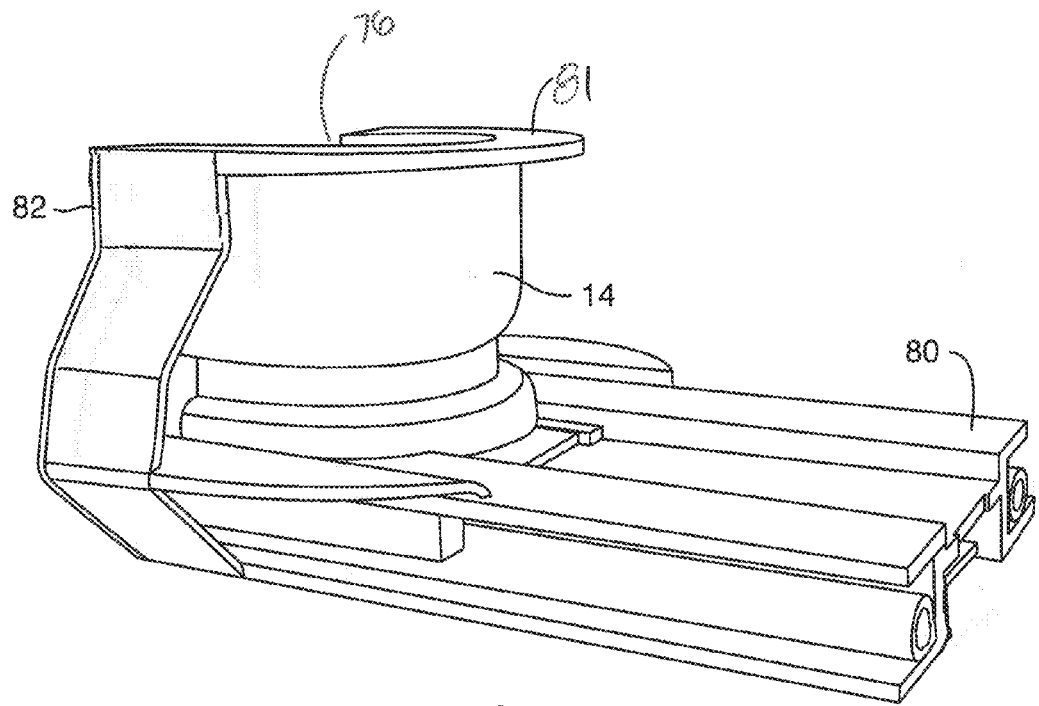
FIG. 7 is a perspective view of an alternate embodiment of an adapter.

FIG. 7 illustrates that particular embodiments of the adapter 14 may also be differently configured at the first end 80 to engage securely with the dispenser 12. FIG. 8 shows the bottom 83 of the adapter 14 and at least one possible positioning of the spring arm 92.

A wide range of dispensers having many different features are suitable for use in the present in invention. A dispenser which utilizes a simple electromechanical mechanism such as a gear train coupled to a driving motor such that a complete rotation of the actuator causes deflection of the spray nozzle and thus a single dispense event.

Figure 9:
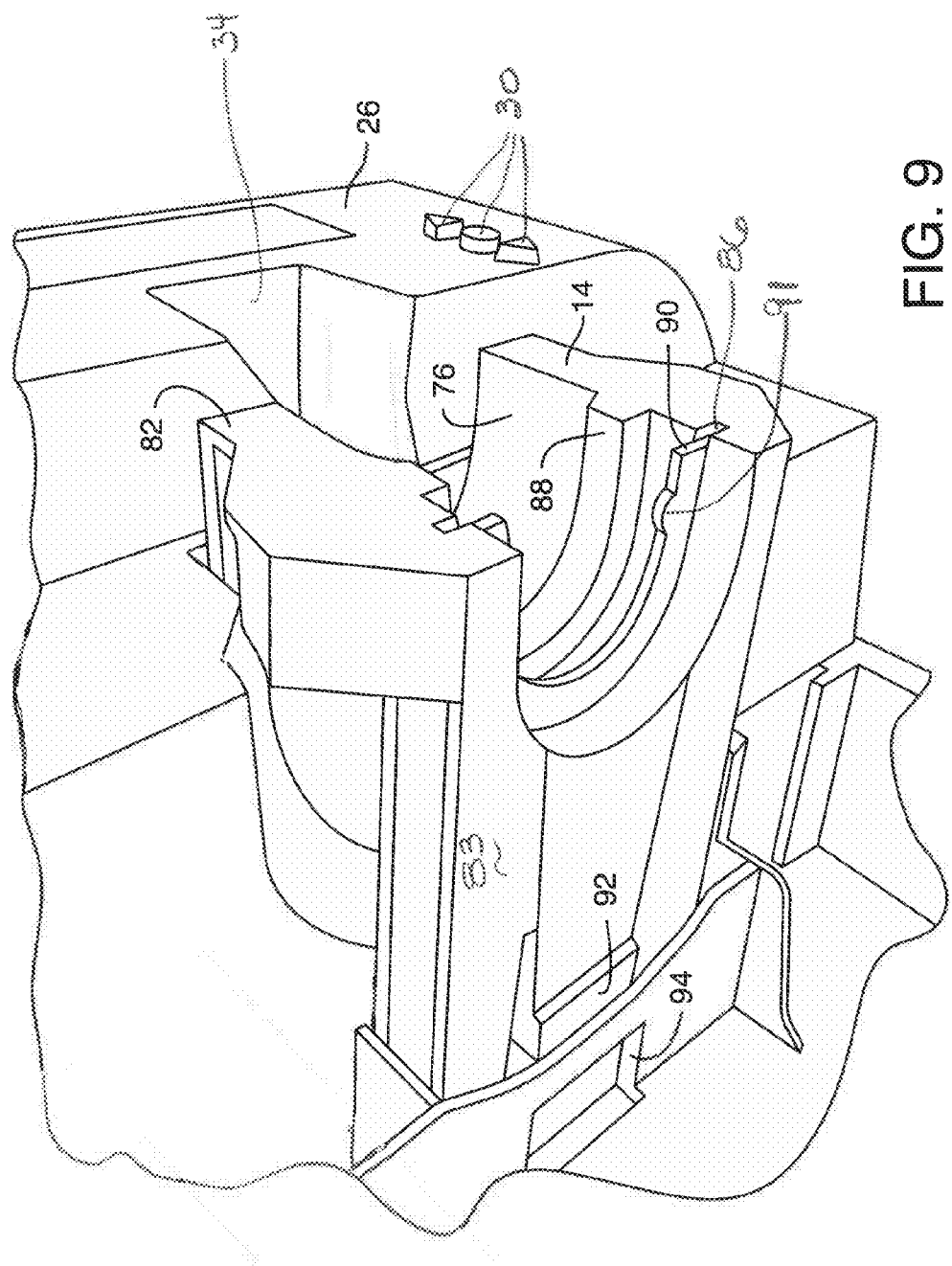
FIG. 9 is a partial perspective view of the adapter and support member shown in FIG. 8 being positioned within the controller.

FIG. 9 is partial perspective view of the adapter and support member shown in FIGS. 7 and 8, the adapter partially engaging the contoured surface 36. To fully seat the adapter 14 within the controller 26, additional force is applied to the end 82 of the adapter 14 to hook the spring arm 92 in the opening 94 and securing the adapter 14 to the controller 26. Of course, the adapter 14 and support member 90 may also be attached to other portions of the dispenser 12.

Figure 10:
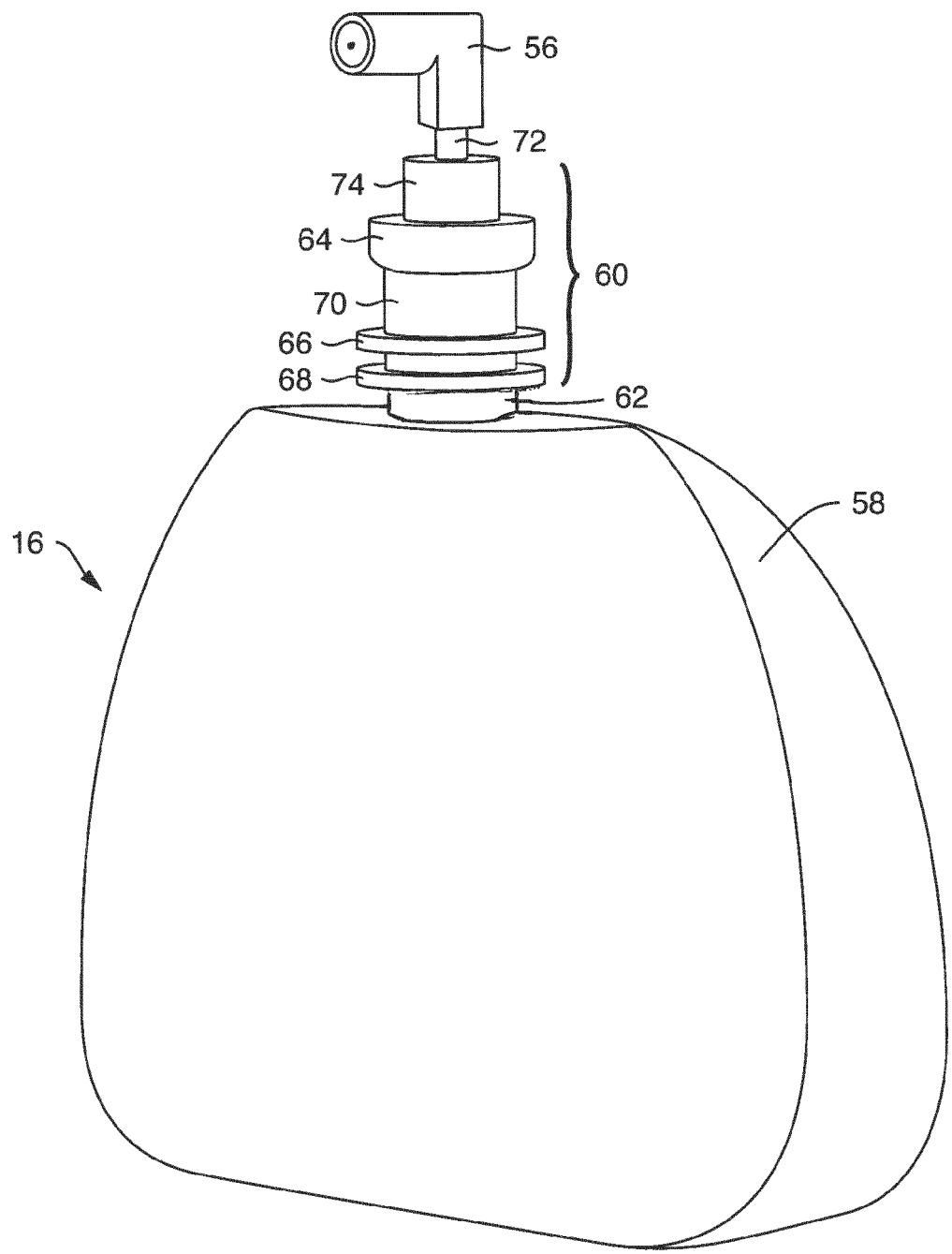
FIG. 10 is a perspective view of a non-aerosol container suitable for use in the present invention.

FIG. 10 illustrates an embodiment of a non-aerosol container 16 including a spray nozzle 56 and a stem 72 extending out of a collar 60. The collar 60 may include an assortment of features that assists the retention of the non-aerosol container 16 in the retention channel 76 of the adapter 14. In the embodiment depicted in FIG. 10, the collar 60 includes three ribs 64, 66 and 68 positioned along a central post 70 that has an end 62. The ribs 64, 66 and 68 may be of different shapes and thicknesses to assist in retaining the non-aerosol container 14 within the collar 60. A reservoir 58 is attached to the collar 60 by any number of conventional methods. While embodiments of the reservoir may differ significantly, the reservoir 58 is preferably a flexible bag which includes the material to be dispensed.

Figure 11:
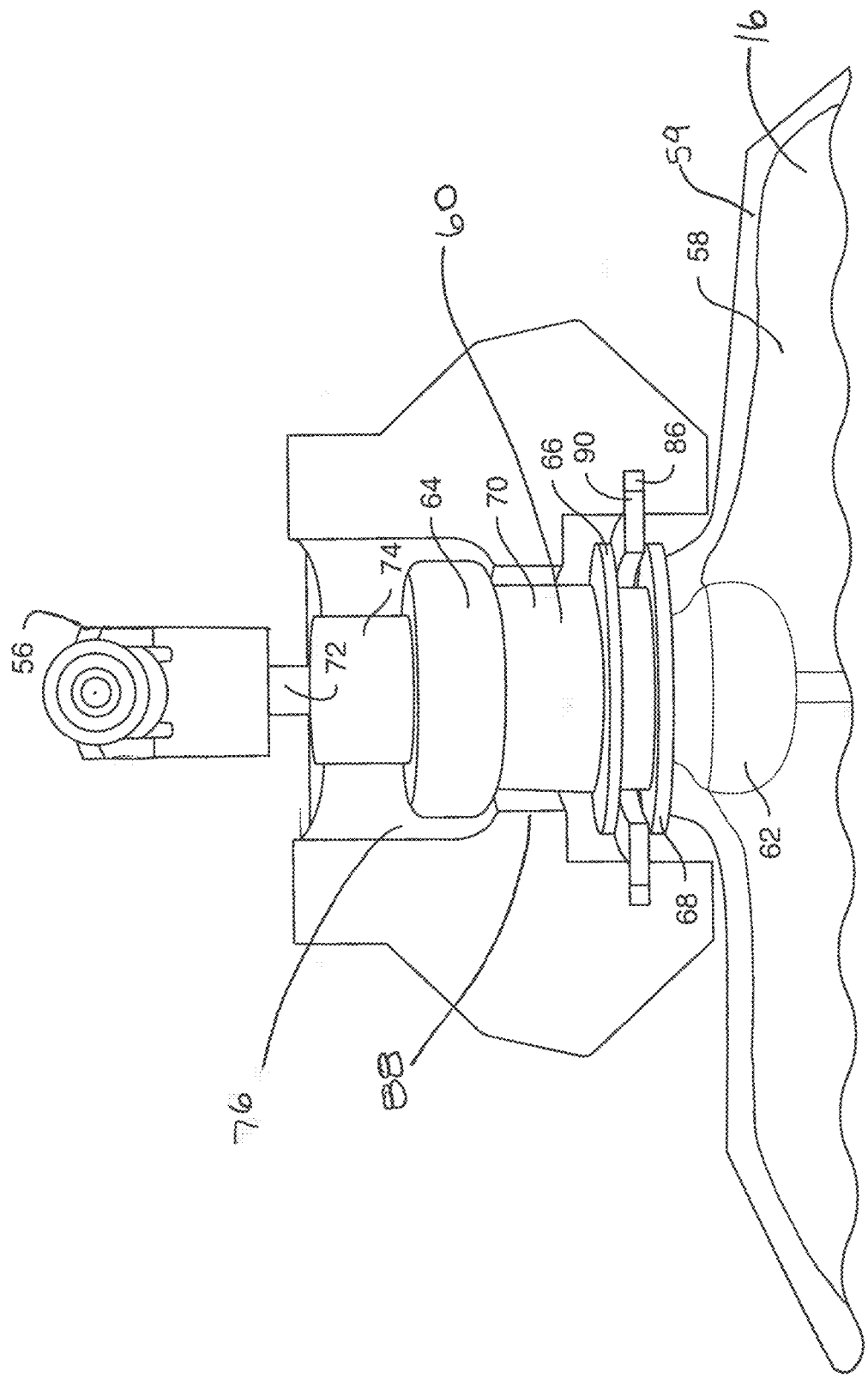
FIG. 11 is a partial view of the a non-aerosol container positioned within an adapter.

FIG. 11 is a partial view of another non-aerosol container 16 having a reservoir 58, collar 60, stem 72 and spray nozzle 56, the non-aerosol container positioned within the adapter 14. Ribs 66 and 68 are positioned on opposite sides of the support member 90. The end 62 of the collar 60 is captured within the reservoir 58 which is formed of a transparent material which is sealed onto the end 62 of the collar 60. The sealed edges 59 of the reservoir 58 are illustrated in FIGS. 11-14.

Different control and actuating mechanisms may be used in the system of the present invention. The dispensers may include a controller 26 which can be used to change factors such as the amount of material dispensed, the time intervals at which the material is dispensed and provide other indications to a user regarding the status of the dispenser 12 such as, for example, power interruptions, low battery notifications and number of dispensing cycles remaining. A user may provide input to the controller via buttons 30 or control panel 32. In some embodiments the control panel 32 may be a display panel.

An exemplary actuating mechanism is shown in FIGS. 12-16, which are front views of the dispenser 12 without the front cover 20 and controller 26. Specifically, FIGS. 12 and 13 are front views of the non-aerosol container 16, the adapter 14, the actuator 32, the selection switch and the dispenser 12. Posts 23, seen in FIGS. 12-16 are configured to attach the front cover 20 to the back cover 22.

The non-aerosol container 16 includes the reservoir 58 having sealed edges 59. The bottom of the reservoir 58 may be supported by the base 24 of the dispenser 12. The adapter 14 is shown attached to the dispenser 12 and the collar 60 is positioned within the retention channel 76.

The actuator 32 is positioned above the adapter 14 and spray nozzle 56 of the non-aerosol container 16. The actuator 32 includes a disk 114 that includes two projections 116 and 118. The disk 114 may rotate in either direction but in the embodiment described in FIGS. 12-16 the disk 114 rotates counter-clockwise.

Figure 16:
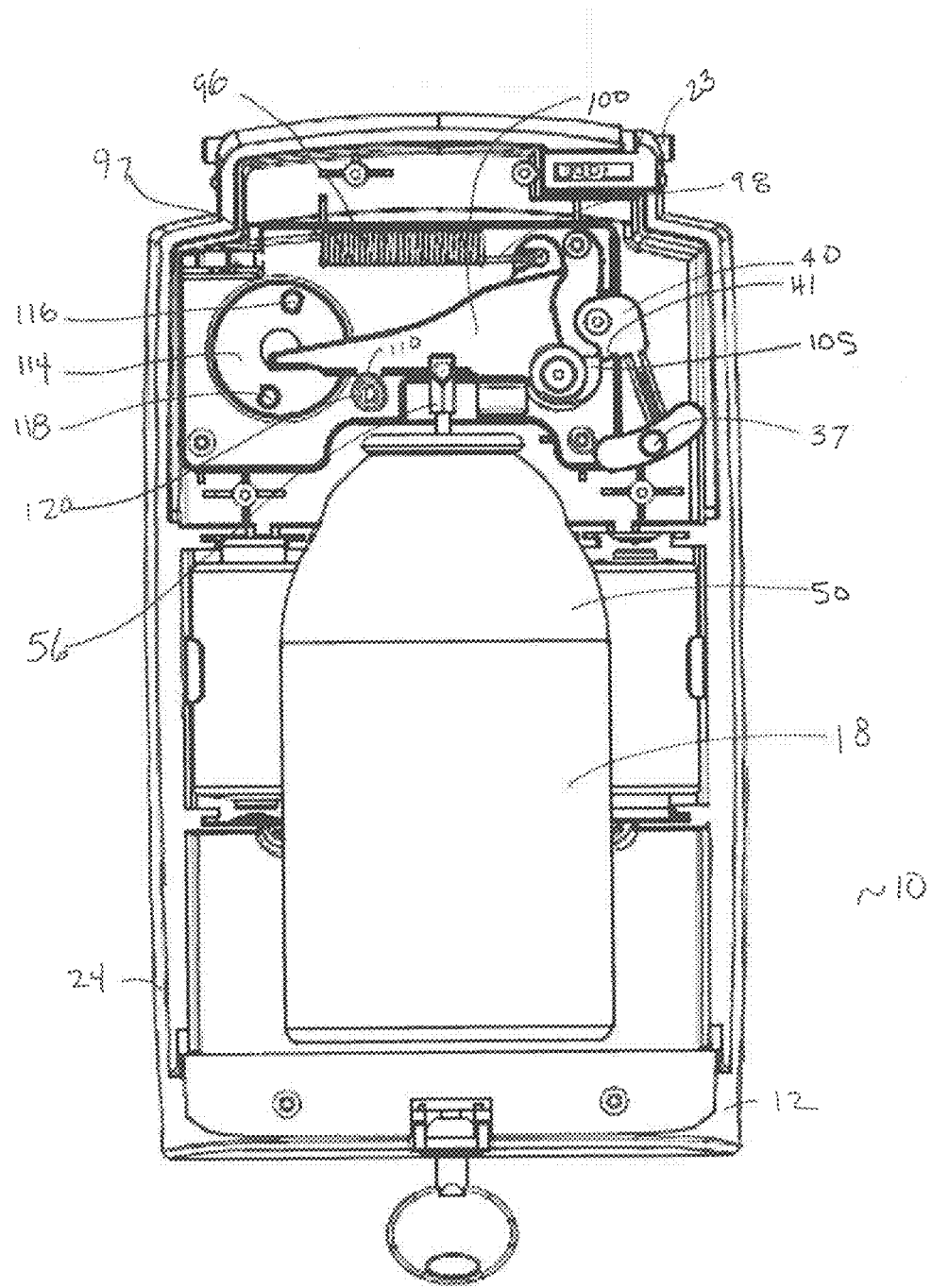

An actuator arm 100 is rotatably secured to the actuator 32 about a pivot point 104. An end 106 of the actuator arm 100 engages the projections 116 and 118 as the disk 114 rotates. As shown in FIG. 12, the end 106 is in contact with the projection 118. Actuating arm 100 further includes a slightly curved ledge 110 which, in selected embodiments and as shown in FIG. 16 engages the stop 120 which is in the form of a cylindrical boss projecting outwardly from the actuator 32. The actuator arm 100 further includes a hammer 108 which is aligned to contact the top surface 57 of the spray nozzle 56 and a stop 105 which is preferably positioned proximate to the selection switch 38.

An aperture 102 is provided above the pivot point 104 of the actuator arm 100. One end of a tension spring 96 is connected to the aperture 102. The other end 97 of the tension spring 96 is fixedly connected to the dispenser 12 so that as the disk 114 rotates and moves the projection 118 out of contact with the end 106 of the actuator arm 100, the spring 96 applies a tensile force to the aperture 102. The tensile force causes the actuator arm 100 to pivot about its pivot point 104 and move the hammer 108 into contact with the upper surface 57 of the spray nozzle 56. The hammer 108 forces the spray nozzle 56 downward, causing material to be dispensed from the reservoir 58 out of the dispenser 12.

To dispense material from a non-aerosol container, the selection switch 38 is to be placed in the non-aerosol position. As seen in FIGS. 12 and 13, the selection switch 38 includes a head 40 that pivots about a pivot point 122. A post 39 connects the head 40 to the button 37. The head 40 includes a ledge 41 that is positioned so that, when the selection switch 38 is moved to the non-aerosol position, the ledge 41 halts the downward motion of the hammer 108 by contacting the stop 105 of the actuator arm 100. This enables two different actuating motions to be embodied in a single actuator, enabling aerosol and non-aerosol containers to be dispensed from a dispenser.

Figure 14:
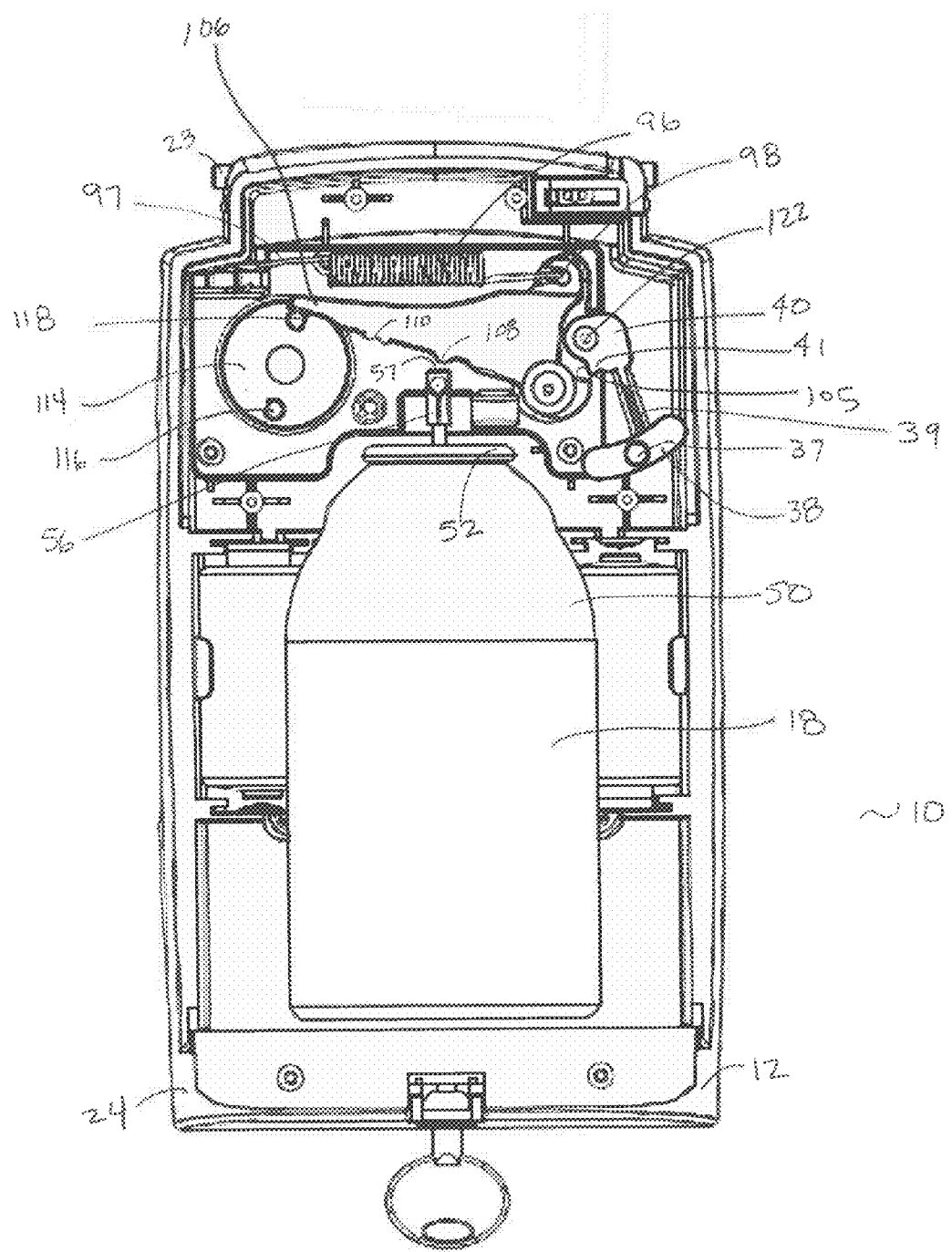
FIGS. 14, 15 and 16 are partial front views of the dispenser system including the dispenser, an aerosol container, an adapter and the actuator.
Figure 15:
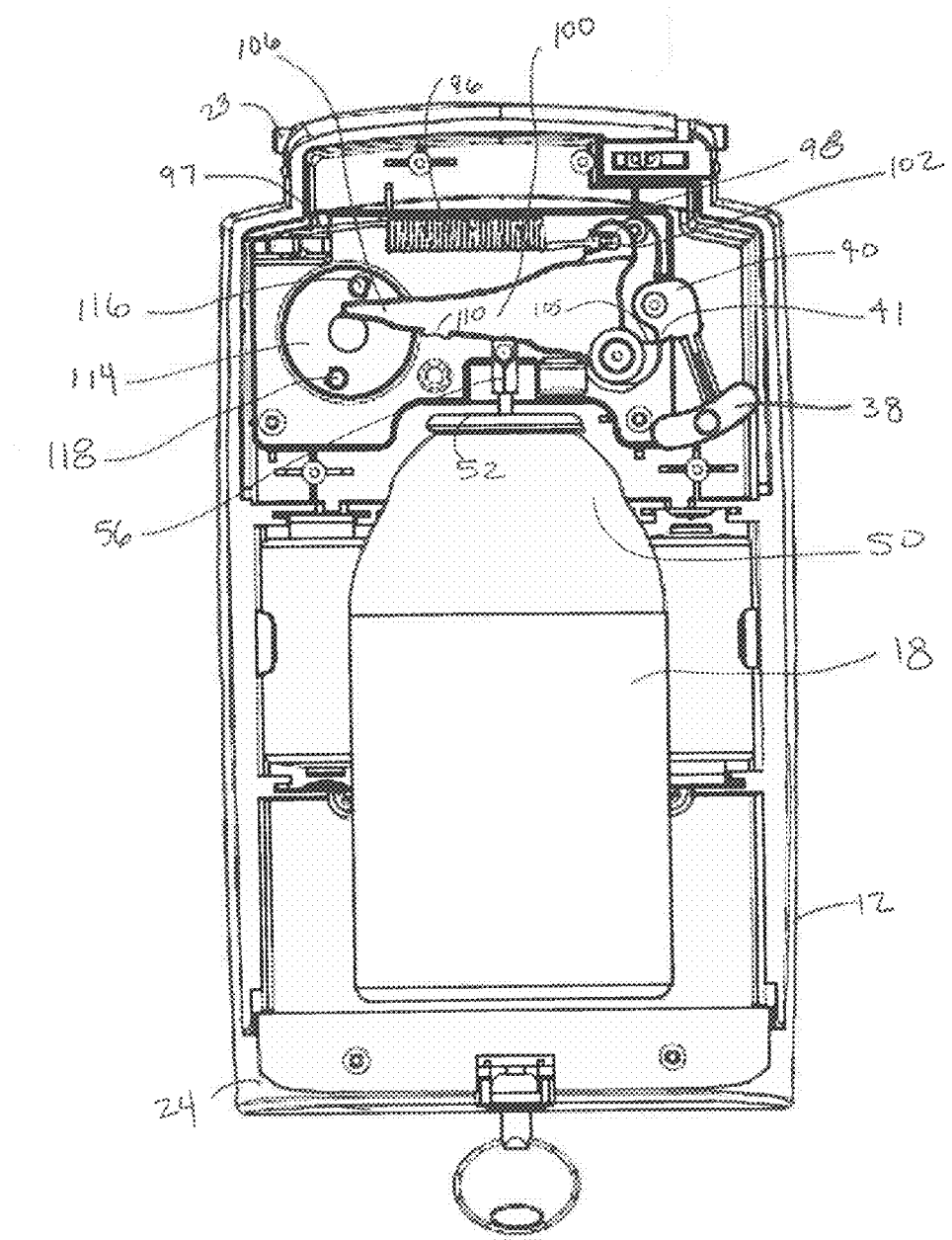

FIGS. 14-16 depict the present invention when dispensing material from an aerosol container 18. The selection switch 38 is positioned in the aerosol position which causes the selection switch 38 to pivot about pivot point 122 causing ledge 41 to move away from the actuator arm 100 and stop 105. Hence, the selection switch 38 does not impede the downward progress of the actuator arm 100 when the selection switch 38 is in the aerosol position. FIG. 14 shows the end 106 of actuator arm 100 resting on stop 118. In FIG. 15, the disk 116 has rotated counter-clockwise permitting the actuator arm 100 to move downward under the tensile force applied by the spring 96. The hammer 108 contacts the spray nozzle 56 moving it downward and activating the flow of material from the aerosol container 18. FIG. 16 shows the arcuate ridge 110 of the actuator arm 100 contacting the stop 120 and preventing the actuator arm 100 from pivoting further.

It should be appreciated by those skilled in the art that various modifications and variations may be made to features of the dispenser described herein, particularly to the mechanical and control circuitry aspects of the dispenser, without departing from the scope and spirit of the invention. It is intended that the invention include all such modifications and variations.

What is claimed is:

1. A dispensing system for air care products contained in aerosol containers and non-aerosol containers, each such container including a spray nozzle, the dispensing system comprising:
   a dispenser including
      an interior formed by a front cover, a back cover and a base,
      an actuator,
      a controller adapted to actuate the actuator;
      a selection switch positionable in an aerosol dispensing position and a non-aerosol dispensing position;
      a contoured surface configured to accept an aerosol container within the interior of the dispenser such that the actuator may contact the aerosol spray nozzle;
   an adaptor configured to be releasably attached to the contoured surface of the dispenser, the adaptor configured to accept a non-aerosol container within the interior of the dispenser such that the actuator may contact the non-aerosol spray nozzle.

2. The dispensing system of claim 1 further comprising a retention mechanism configured to releasably connect the adaptor to the contoured surface of the dispenser.

3. The dispensing system of claim 2 wherein the retention mechanism includes a spring arm and an opening formed in the dispenser, the spring arm being positioned on the adaptor.

4. The dispensing system of claim 1 wherein the actuator includes an actuator arm positioned above the spray nozzle and wherein the actuator arm contacts the spray nozzle as the actuator arm moves downward.

5. The dispensing system of claim 4 wherein the selection switch in the non-aerosol dispensing position contacts the actuator arm to limit the downward movement of the actuator arm.

6. The dispensing system of claim 1 wherein the adaptor further includes a retainer for positioning the non-aerosol container within the dispenser.

7. The dispensing system of claim 1 wherein the controller is adapted to actuate the actuator at predetermined time intervals.

8. The dispenser system of claim 1 further including a non-aerosol container positioned at least partially within the adaptor.

9. The dispenser system of claim 1 wherein the dispenser system is capable of dispensing material from a non-aerosol container positioned at least partially within the adaptor while the adaptor is retained within the contoured surface and when the selection switch is positioned in the non-aerosol dispensing position.

* * * * *